United States Patent
O'Donnell, Jr.

(10) Patent No.: US 6,562,027 B2
(45) Date of Patent: May 13, 2003

(54) METHOD AND APPARATUS FOR IMPROVED PRK ACCURACY

(76) Inventor: Francis E. O'Donnell, Jr., 709 The Hamptons La., Town & Country, MO (US) 63017

(*) Notice: Subject to any disclaimer, the term of this patent is extended or adjusted under 35 U.S.C. 154(b) by 43 days.

(21) Appl. No.: 09/741,132

(22) Filed: Dec. 19, 2000

(65) Prior Publication Data

US 2001/0003154 A1 Jun. 7, 2001

Related U.S. Application Data

(63) Continuation-in-part of application No. 08/910,085, filed on Aug. 12, 1997.
(60) Provisional application No. 60/024,523, filed on Aug. 26, 1996.

(51) Int. Cl.$^7$ .................................................. A61F 9/007
(52) U.S. Cl. ............................ 606/12; 606/3; 606/10; 606/13
(58) Field of Search ............................... 606/3–6, 10–17

(56) References Cited

U.S. PATENT DOCUMENTS

| | | |
|---|---|---|
| 4,669,466 A | 6/1987 | L'Esperance |
| 4,732,148 A | 3/1988 | L'Esperance, Jr. |
| 4,773,414 A | 9/1988 | L'Esperance, Jr. |
| 4,911,711 A | 3/1990 | Telfair et al. |
| 5,108,412 A | 4/1992 | Krumeich et al. |
| 5,163,934 A | 11/1992 | Munnerlyn |
| 5,395,356 A | 3/1995 | King et al. |
| 5,549,599 A | 8/1996 | Sumiya |
| 6,210,169 B1 * | 4/2001 | Yavitz ............................ 606/5 |

* cited by examiner

Primary Examiner—David M. Shay
(74) Attorney, Agent, or Firm—Paul M. Denk

(57) ABSTRACT

A method for enhancing the accuracy of PRK wherein a UV power meter is placed in the optical path of the laser beam. In one preferred embodiment, the power meter is placed distal to the last optical element so that any optical degradation that affects laser performance is taken into account. The meter consists of a UV-B cube and a pulnix camera with a software package. The meter is used to monitor the fluence of each laser pulse. The power meter is used to size each pulse and to quantify the energy in each pulse. Sensing means is employed to measure intraoperative pulse-to-pulse energy during photorefractive keratectomy (PRK), using said data in conjunction with the location of the pulse within the ablation zone to determine the cumulative energy thus being achieved, and adjusting said laser to treat more or less at each point based upon the difference between the ideal cumulative energy map and the observed cumulative energy map derived from intraoperative power determination.

5 Claims, 5 Drawing Sheets

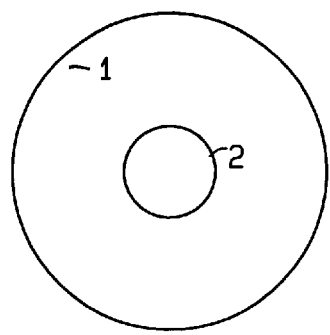
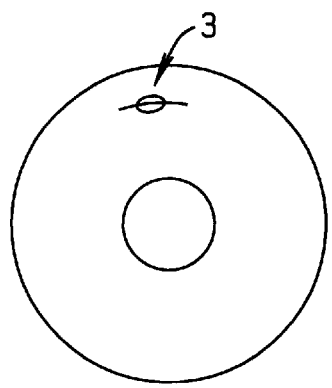
FIG. 8A
FIG. 8B
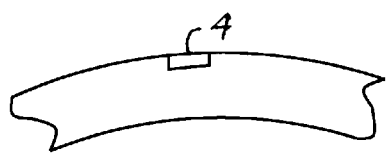
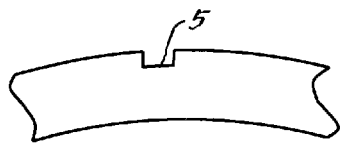
FIG. 8C
FIG. 8D
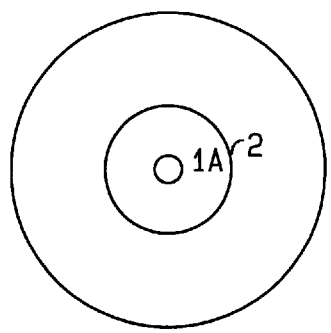
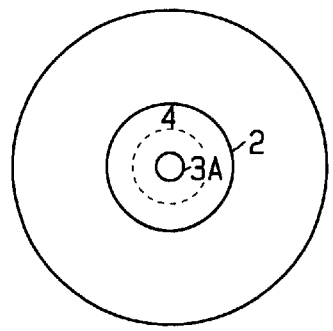
FIG. 9A
FIG. 9B
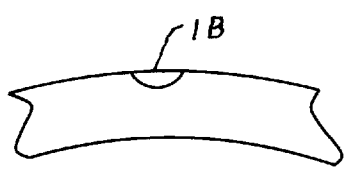
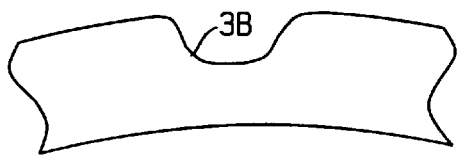
FIG. 9C
FIG. 9D

METHOD AND APPARATUS FOR IMPROVED PRK ACCURACY

CROSS REFERENCE TO RELATED APPLICATIONS

This application is a continuation-in-part of application Ser. No. 08/910,085 filed Aug. 12, 1997, which claims priority on the provisional application patent application Serial No. 60/024,523, filed Aug. 26, 1996 by the same applicant.

BACKGROUND OF THE INVENTION

Photorefractive keratectomy (PRK) with pulsed ultraviolet or pulsed infrared laser has limited accuracy, in part, because of pulse-to-pulse power fluctuation of as much as 8%. As disclosed in the prior art patent to L'Esperance, U.S. Pat. No. 4,669,466, there is shown the usage of corneal topography to guide the ablation process. Specifically, a videokeratographic topography apparatus is used to determine the physical, three-dimensional shape of the ablation and this is compared to an ideal ablation profile.

Telfair in U.S. Pat. No. 4,911,711 described the use of a beam profiler means to monitor the homogeneity of the energy profile of individual pulses. In addition, like L'Esperance, Telfair taught the use of intraoperative corneal topography ("surface diagnostics") to help guide the ablation process. Later, King in U.S. Pat. No. , 5,395,356 taught the use of "a measuring device is included within the apparatus for measuring a parameter which is a function of the corneal surface, such as refractive power or surface curvature."

In fact, since it has been difficult to accurately measure the ablation profile on the cornea during or at the end of the treatment, there has been no way to ensure that the desired ablation profile has been achieved in the individual case until many days after treatment. This allows for unwanted overcorrections and undercorrections, requiring retreatment.

In addition to variable pulse energy (fluence), another factor that interferes with PRK accuracy is individual variation in etch rate (amount of tissue removed per pulse for a given energy level). That is to say, that the corneas of some patients ablate slower or faster than the average. Prior art has demonstrated that dry corneal tissue ablates faster than "wet" corneal tissue. It is believed that water absorbs the laser energy making it less effective in the removal of corneal tissue. Prior art attempts to measure the actual ablation depth achieved in the individual patient have relied upon corneal topography-type technology and ultrasonic pachymetry, both of which have been very inaccurate and difficult to perform intraoperatively.

SUMMARY OF THE INVENTION

It is the principle object of this invention to provide method and means for furnishing extreme accuracy in the ablation profile during performance of the PRK procedure through the use of an energy or power metering means located within the optical path of the laser beam to furnish an actual assessment of the laser energy delivered with each pulse, allowing creation of an energy map used as a reference to indicate the amount and degree of ablation occurring during actual performance of the PRK procedure.

The present invention monitors intraoperative laser energy of each pulse and records the total energy delivered at each point within the ablated area on the cornea. It allows for construction of topography maps of the ablation area based upon energy delivered, rather than actual measurement of the surface of the ablation as taught in prior art. It can be used to prevent overcorrections and undercorrections, reducing potential patient dissatisfaction. Moreover, the present invention adjusts the etch rate (ablation rate) to take into account individual variation in corneal hydration, using the etch rate (ablation rate) to more accurately interconvert the energy map and the physical topography map.

A UV power meter is placed in the optical path of the laser beam. In a preferred embodiment, the power meter is placed distal to the last optical element so that any optical degradation that affects laser performance is taken into account. (FIG. 1). The power meter can be obtained from Coherent, Inc. located in Auburn, Calif., 95602. This meter consists of a UV-B cube and a pulnix camera with a software package developed by Coherent. It can be used in the present invention to monitor the fluence of each laser pulse. Unlike prior art which uses a power meter to profile the energy homogeneity, this power meter is used to size each pulse and to quantify the energy in each pulse.

It is, therefore, an object of this invention to provide sensing means to measure intraoperative pulse-to-pulse energy during photorefractive keratectomy (PRK), using said data in conjunction with the location of the pulse within the ablation zone to determine the cumulative energy thus being achieved, and adjusting said laser to treat more or less at each point based upon the difference between the ideal cumulative energy map and the observed cumulative energy map derived from intraoperative power determination.

Still another object of this invention is to provide means for placement of the sensing means previously referred to, by spatially locating the sensing means distal in the optic train of the laser system.

Still another object of this invention is to provide for the automatic termination of additional laser treatment to all or part of the ablation zone through usage of a sensing means that provides an analysis of the difference between the theoretic cumulative laser energy targeted and the observed cumulative energy map derived from the intraoperative power determination.

Still another object of this invention is to provide automatic delivery of additional laser pulses to all or part of the ablation zone through usage of the sensing means of this invention.

Yet another object of this invention is to provide for adjustment of the etch rate that takes into account the effects of corneal hydration during photorefractive keratectomy.

Still another object of this invention is to provide for an assessment of the corneal hydration through the use of central corneal pachymetry used during performance of the PRK process.

Yet another object of this invention is to provide intraoperative determination of ablation depth.

Yet another object of this invention is to provide for the use of individualized etch rate to compensate for the effects of corneal hydration for use for interconverting the energy map derived from the sensing means to derive a physical topography map of the cornea during performance of the PRK process.

BRIEF DESCRIPTION OF THE DRAWINGS

FIG. 8a shows a front view of a peripheral, superficial stab incision;

FIG. 8b shows a test ablation which straddles the previously applied incision;

FIG. 8c is a sagittal view disclosing the marked incision;

FIG. 8d shows the marked incision after the dye disappears;

FIG. 9a shows a laser aiming beam focused on the surface of the corneal stroma following epithelial removal;

FIG. 9b shows the measurement of the aiming beam after a known number of pulses have been delivered;

FIG. 9c provides a sagittal view of the surface spot size being altered; and

FIG. 9d discloses the depth of the ablation.

DESCRIPTION OF THE PREFERRED EMBODIMENT

Figure 1:
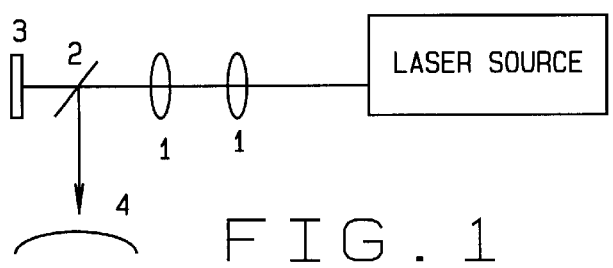
FIG. 1 provides a schematic of the laser source, during performance of PRK, with the location of the fluence sensing means arranged in line with the generated laser beam.

In this invention, utilizing a UV power meter located within the optical path of the laser beam, as can be seen in FIG. 1 provides critical information on pulse energy and size. The power meter is located at the more distant extent of the laser beam as can be noted at 2. FIG. 1 discloses the potential location for the preference for the location 2 as distal to most or all of the laser optics, taking into account their effects on the pulse power. The optics 1 as noted for the laser beam provide for focusing, shaping, and homogenizing of the beam upon its delivery to the patient's cornea (4) during performance of the PRK process. The laser source, obviously, provides the source for generation of the laser, and the reflective mirror 2 provides for an angular redirection of the laser beam during its projection. Mirror 2 is only partially (e.g. 95%) reflective, allowing power meter 3 to sample the output energy and pulse size in order to determine the fluence of laser pulse.

Figure 2:
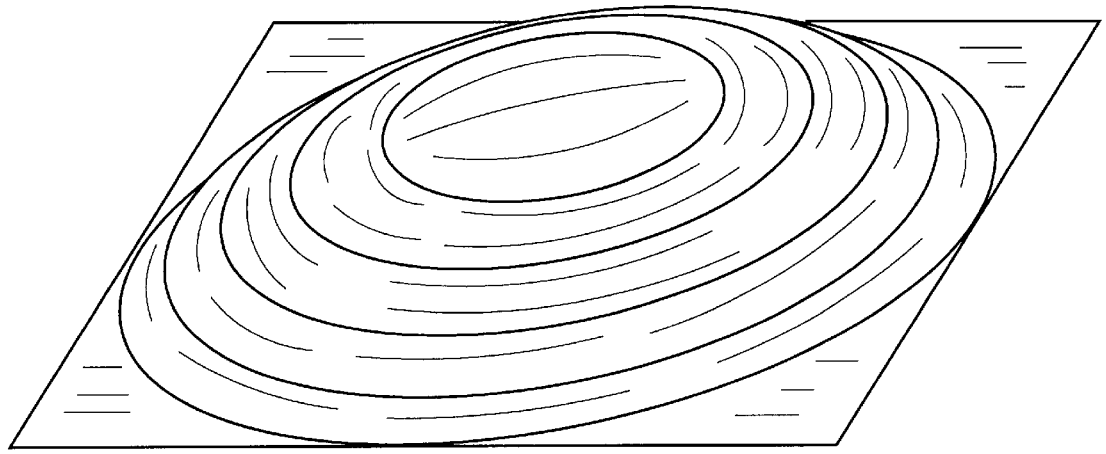
FIG. 2 is a three-dimensional energy map showing the targeted cumulative energy at each point in the ablation.
Figure 3:
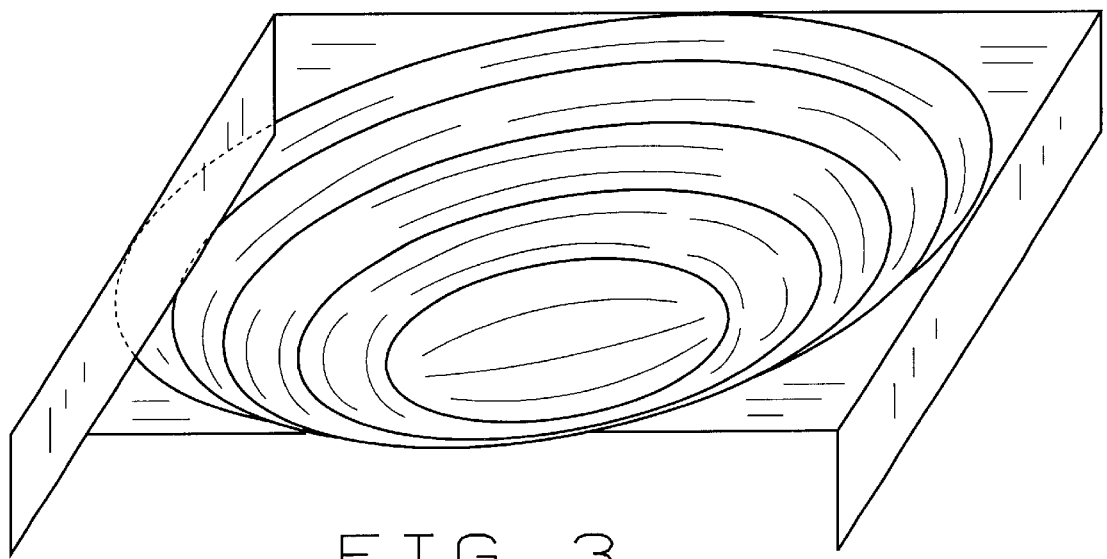
FIG. 3 is a three-dimensional corneal topography of the PRK ablation profile that would be generated from FIG. 2 using equation (1).

In one preferred embodiment, the targeted energy map is represented in a three-dimensional display as in FIG. 2. This targeted energy map can be derived from the targeted PRK ablation profile, as shown in FIG. 3, by using equation (1) which is a useful approximation.

$$Vol_p = \Sigma^x_{N=0} \pi r_N^2 (kf_N) H \quad (1)$$

At any given point (p) in the ablation wherein $Vol_p$ is the volume of corneal tissue ablated at a point p, r=radius of the $N^{th}$ pulse, x is the total number of pulses at point p, the product $(kf_N)$ is equal to the ablation depth of pulse number N, K is a constant for a given laser system, $f_N$ is the fluence of pulse number N. H is the effects on ablation rate associated with hydration state (water content). From this equation, it is possible to calculate a targeted energy map from a desired PRK ablation profile. The ablation profile is a corneal topography difference map (i.e., preoperative corneal topography minus postoperative corneal topography).

Figure 4:
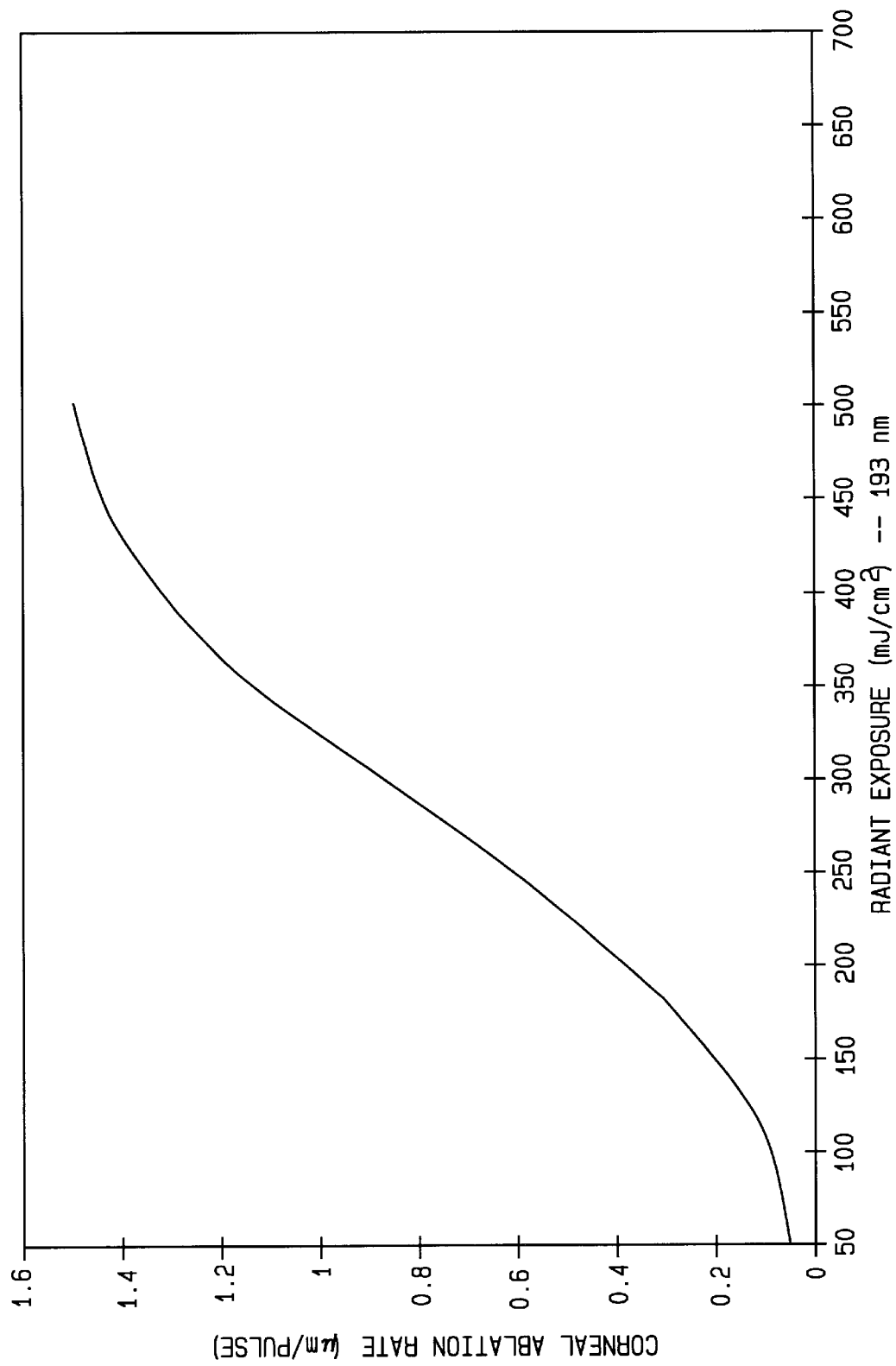
FIG. 4 is a prior art representation of the quasi-linear relationship between ablation rate in corneal tissue and fluence.

From prior art, the relationship between fluence and ablation rate in cornea was thought to be somewhat linear in the fluence range used clinically as shown in FIG. 4. I have determined that this relationship depends upon the exact laser system used (k). Specifically, the ablation rate is inversely proportional to the square of the pulse diameter. That is to say, larger spot sizes are significantly less ablative than smaller spot sizes. For example, at the same fluence, iris diaphragm delivery systems ablate corneal tissue approximately 50% less effectively than a 1 mm in diameter scanned spot. Some of this wasted energy is dissipated in the photoacoustic shockwave and thermal side effects of large spots. Using a volumetric analysis of PRK ablations and the energy map of the present invention, I have determined that the energy expended to ablate each cubic micron of corneal tissue is not predicted by prior art. Thus, my constant K corrects for the laser system's effects on ablation efficiency. This insight yields an improved correlation between energy map and corneal topography map. Thus equation (1) provides for an interconversion of energy map and corneal topography of the ablation.

In addition to discovering an improved way to predict ablation rate based upon the laser system selected, I have determined that the ablation rate's known dependence upon corneal hydration can be used to improve the accuracy of PRK. Specifically, prior art has not quantified the effects of corneal hydration on the ablation rate. I have determined several means to quantify the hydration effects in any given cornea, adjusting the ablation efficiency in equation (1) by factor H. These means are more fully disclosed below, but here it is sufficient to characterize them as providing an individualized ablation rate, thus improving the predictive value of the energy map of the present invention.

Figure 5:
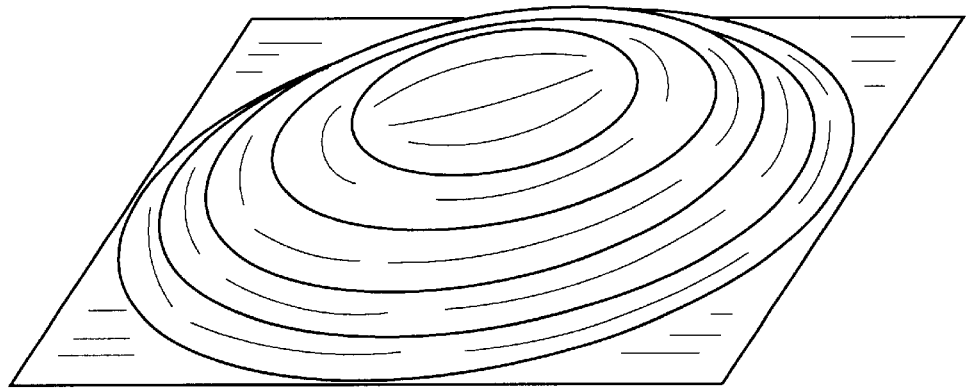
FIG. 5 is a three-dimensional energy map showing the actual (observed) cumulative energy at each point in the ablation.
Figure 6:
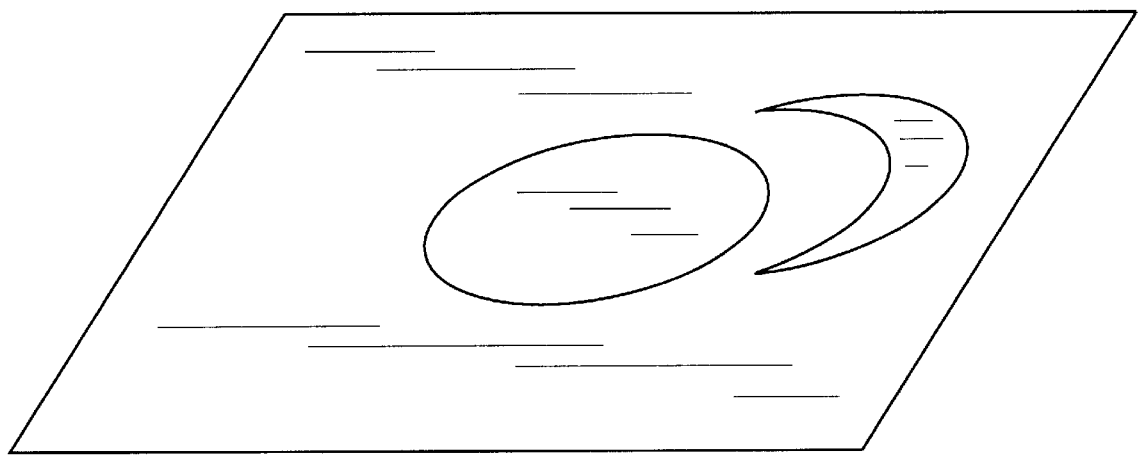
FIG. 6 is a difference energy map showing an area of undercorrection in the central ablation.

In one preferred embodiment, FIG. 5 shows the three-dimensional representation of the actual (observed) cumulative energy map at each point in the ablation. FIG. 6 is a difference energy map (i.e., FIG. 2 energy map minus FIG. 5 energy map) showing an area of undercorrection in the central part of the ablation. As can be further noted in FIG. 6, the difference of the observed cumulative energy map and the theoretical (targeted) energy map shows the deviation (difference map) from the theoretical cumulative energy map in a spatially-resolved fashion.

In another preferred embodiment, the computer controlling the laser PRK ablation can be programmed so as to automatically stop further ablation in all or part of the ablation area once a predetermined cumulative ablation energy is achieved in order to avoid overcorrection.

In another preferred embodiment, the computer controlling the PRK ablation can be programmed to automatically provide more pulses to the area (or part of the area) of the ablation if the cumulative energy per point indicates an undercorrection.

In another preferred embodiment, the power meter input is used to automatically adjust the electrical current in the laser source so as to minimize the deviation from the desired power for each pulse.

In another preferred embodiment, the etch rate (ablation rate) used to interconvert the energy map and the three-dimensional physical topography map is adjusted to compensate for differences in ablation rate amongst individual patients. It has been determined that there is significant variation in the amount of tissue ablated for the same energy level per pulse amongst individuals. I have determined that this difference is due primarily to differences in the hydration state of the cornea. One measure of the hydration state of the cornea is through the use of ultrasonic means. For example, using a 50 mHz probe, it has been determined that slower ablating corneas have a lower etch rate that is inversely proportional to the corneal hydration which, in turn, is directly proportional to the central corneal thickness as can be noted in FIG. 7.

Figure 7:
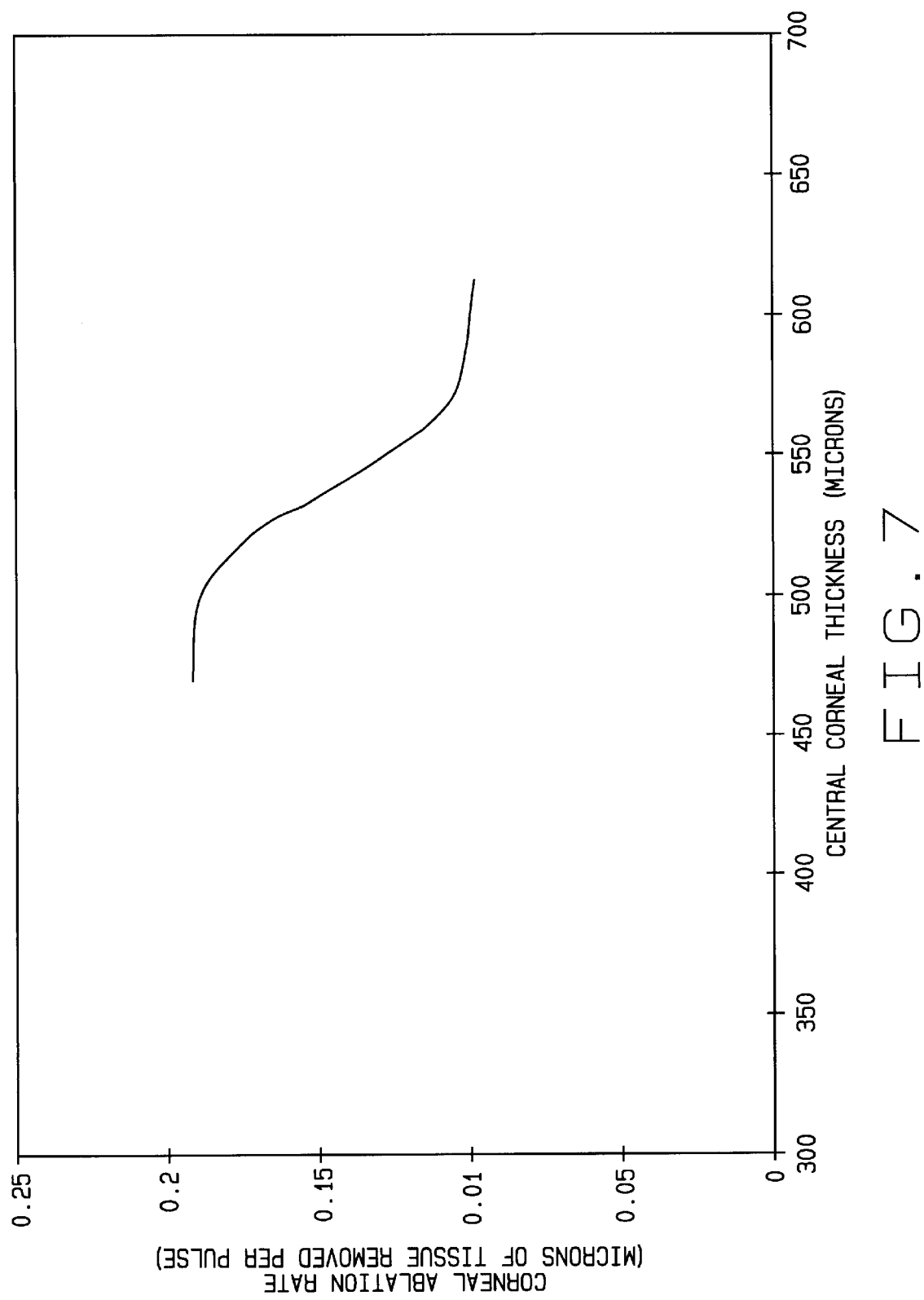
FIG. 7 provides a chart comparing etch rate to the central corneal thickness to derive the PRK etch rate and the effects of corneal hydration during performance of the PRK process.

As can be observed from the chart of FIG. 7, the central corneal thickness is proportional to corneal hydration. Increasing the corneal hydration reduces the PRK etch rate, that is, the amount of tissue ablated per pulse.

In another preferred embodiment, the corneal etch rate is determined for each patient by performing a peripheral, shallow ablation far removed from the central cornea (FIG. 8). The predetermined depth is established by penetrating the peripheral cornea with a small diamond blade advanced to a predetermined depth by micrometer device, the tip preferably dipped in methylene blue or other medically useful dye, and straddling the puncture site with the pulses. The individual corneal etch rate is determined by dividing the depth by the number of pulses necessary to remove all traces of the dye.

In referring to FIG. 8, this shows the frontal view of a peripheral, superficial stab incision, as made at 1, performed with a diamond knife to a depth known as controlled by a micrometer advance. The diamond knife tip is dipped in a dye to enhance visualization. The incision is made in the peripheral cornea far from the pupil 2. The test ablation, as at 3, straddles the incision. As seen on a sagittal view, as at 4, the marked incision is ablated until the dye disappears, as shown at 5.

Yet another means to measure the etch rate is the placement preoperatively of an Nd:YAG or other laser spot at a predetermined depth in the central cornea. In a related patent (U.S. Pat. No. 5,507,740), I disclose the use of a hydrophobic thin membrane to allow corneal topography of the ablated surface. From the determinant of central ablation depth, the etch rate can be derived.

In another preferred embodiment, the effective etch rate is determined by measuring the central ablation depth for a known number of central pulses. Projection of a divergent or convergent helium-neon or diode aiming beam onto the stromal surface after the subsequent placement of a known number of central pulses allows determination of etch rate by measurement of spot size at the bottom of the ablation (FIG. 9). For example, with a divergent He-neon beam, the size of the spot is proportional to the ablation depth. Alternatively, intersecting laser aiming beams can be used such that the distance between the two spots is a measure of ablation depth. That is to say, the beams intersect to form a single spot at the unablated corneal surface, but when the ablation proceeds, the beams diverge in the depths of the ablation.

In reviewing FIG. 9, a laser aiming beam of precise, known size, as at 1A, is focused on the surface of the corneal stroma following epithelial removal, as at 2. After a known number of pulses are delivered, the size of the aiming beam, as at 3A, is measured; and it is used to determine the central ablation depth because its size is known proportional to the ablation depth at the center of the PRK, as at 4. On sagittal views, the surface spot size, as at 1B, is seen to be altered, as at 3B, by the depth of the ablation.

Variations or modifications to the subject matter of this development may occur to those skilled in the art upon reviewing the summary herein and undertaking a study of the description of the preferred embodiment in light of the drawings. Such variations or modifications, if within the spirit of this invention, are intended to be encompassed within the scope of this development and disclosure.

What is claimed is:

1. A method for improving the accuracy of photorefractive keratectomy for a laser during ophthalmological surgery upon a patient, comprising:

identifying a photorefractive keratectomy ablation profile topography for the patient's eye;

converting said photorefractive keratectomy ablation profile topography into a targeted energy map based upon a predetermined ablation rate for the laser;

applying a UV power meter in the optical path of the laser beam for measuring of the laser pulse energy;

applying a UV power meter in the optical path of the laser beam for measuring of the laser pulse size;

applying a UV power meter in the optical path of the laser beam for measuring a laser pulse location during performance of an ablation upon the patient's eye, the ablation rate determined by measuring of a size of a convergent or divergent last spot, before and after a known number of laser pulses are conducted;

summating the total energy measured at each location in said ablation;

creating a three-dimensional map of the measured energy delivered during the performance of photorefractive keratectomy upon the patent's eye;

comparing the targeted energy map and the measured energy map; and for areas of the patient's eye with measured energy below the targeted energy, applying more laser pulses until the measured energy equals the targeted energy.

2. The method of claim 1 wherein the ablation rate is determined by measuring a distance between two intersecting laser beams before and after a known number of laser pulses are conducted.

3. The method of claim 1 wherein the actual energy delivered with each pulse is measured at a last reflective optic component before the laser impinges the cornea of the patient's eye.

4. The method of claim 1 wherein the ablation rate is determined by measuring central corneal thickness pretreatment.

5. The method of claim 1 wherein the ablation rate is determined by measuring the number of pulses required to achieve ablation of a corneal intrastromal target of predetermined depth, wherein the intrastromal target is selected from the group comprising a dye, or a Nd:YAG laser lesion.

* * * * *